(12) United States Patent
Meeks et al.

(10) Patent No.: US 8,823,935 B1
(45) Date of Patent: Sep. 2, 2014

(54) DETECTING AND CLASSIFYING SURFACE DEFECTS WITH MULTIPLE RADIATION COLLECTORS

(75) Inventors: Steven W. Meeks, Fremont, CA (US); Xiaoqian Xu, San Jose, CA (US); Hung P. Nguyen, Santa Clara, CA (US); Alireza Shahdoost Moghadam, San Jose, CA (US); Mahendra Prabhu Ramachandran, Palo Alto, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 664 days.

(21) Appl. No.: 12/556,596

(22) Filed: Sep. 10, 2009

Related U.S. Application Data

(60) Provisional application No. 61/095,801, filed on Sep. 10, 2008.

(51) Int. Cl.
*G01N 21/00* (2006.01)
(52) U.S. Cl.
USPC .......................... 356/369; 356/237.4; 356/600
(58) Field of Classification Search
USPC ............ 356/369, 237.2–237.6, 600, 337–343
See application file for complete search history.

(56) References Cited

U.S. PATENT DOCUMENTS

| | | | |
|---|---|---|---|
| 5,245,403 A * | 9/1993 | Kato et al. | 356/239.8 |
| 5,798,829 A | 8/1998 | Vaez-Iravani | |
| 6,034,776 A | 3/2000 | Germer et al. | |
| 6,201,601 B1 | 3/2001 | Vaez-Iravani et al. | |
| 6,384,910 B2 | 5/2002 | Vaez-Iravani et al. | |
| 6,639,662 B2 | 10/2003 | Vaez-Iravani et al. | |
| 6,657,715 B2 | 12/2003 | Vaez-Iravani et al. | |
| 7,061,601 B2 | 6/2006 | Meeks | |
| 7,110,106 B2 * | 9/2006 | Xu et al. | 356/237.5 |
| 7,190,447 B2 | 3/2007 | Meeks | |
| 7,206,066 B2 * | 4/2007 | Vurens et al. | 356/237.2 |
| 7,755,752 B1 * | 7/2010 | Salnik et al. | 356/237.2 |
| 2008/0144023 A1 * | 6/2008 | Shibata et al. | 356/237.2 |

* cited by examiner

*Primary Examiner* — Gregory J Toatley
*Assistant Examiner* — Rebecca C Bryant
(74) *Attorney, Agent, or Firm* — Luedeka Neely Group, P.C.; Rick Barnes

(57) ABSTRACT

A system to detect and classify defects on a surface of a substrate. A first targeting assembly directs radiation in a first beam onto the substrate. A first collecting assembly collects first radiation specularly reflected from the substrate and produces first signals, a second collecting assembly collects first radiation scattered from the surface of the substrate by defects and not micro-roughness and produces second signals, and a third collecting assembly collects first radiation scattered from the surface of the substrate by defects and micro-roughness and produces third signals. A second targeting assembly directs radiation in a second beam onto the substrate. A fourth collecting assembly collects second radiation scattered from the substrate and produces fourth signals. A processor receives the first, second, third, and fourth signals. A module coupled to the processor has logic instructions stored in a computer-readable medium, which configure the processor to analyze the signals to detect and classify the defects on the substrate.

10 Claims, 6 Drawing Sheets

DETECTING AND CLASSIFYING SURFACE DEFECTS WITH MULTIPLE RADIATION COLLECTORS

This patent application claims all rights in and priority to U.S. provisional patent application Ser. No. 61/095,801 filed 2008, Sep. 2010, the entirety of the disclosure of which is incorporated herein by reference. This invention relates to the field of fabrication of magnetic storage media for digital information. More particularly, this invention relates to inspecting the surfaces of such media for defects.

FIELD

Background

Flatness and other surface conditions of the substrates on which magnetic media is formed, and the flatness and condition of the media upon completion, are important characteristics of the media. For example surface defects such as particles and pits can impair the functionality of the media for certain applications. Therefore, media substrates are inspected to determine the existence of such defects, and to try to determine the cause of those defects.

Various optical testing components and techniques for surface inspection are described in U.S. Pat. Nos. 7,190,447, 7,061,601, 6,657,715, 5,798,829, 6,201,601, 6,384910, 6,639,662, and 6,034,776, the disclosures of which are incorporated herein by reference in their entirety. These patents describe differentiating defects such as pits and particles. However, they do not describe differentiating flat particles or shallow dips in the surface of a substrate from pits and spherical or non-spherical particles.

What is needed, therefore, is a system that overcomes limitations such as those described above, at least in part.

SUMMARY

The above and other needs are met by a system to detect and classify defects on a surface of a substrate. A first targeting assembly directs radiation in a first beam onto the substrate. A first collecting assembly collects first radiation specularly reflected from the substrate and produces first signals, a second collecting assembly collects first radiation scattered from the surface of the substrate by defects and not micro-roughness and produces second signals, and a third collecting assembly collects first radiation scattered from the surface of the substrate by defects and micro-roughness and produces third signals. A second targeting assembly directs radiation in a second beam onto the substrate. A fourth collecting assembly collects second radiation scattered from the substrate and produces fourth signals. A processor receives the first, second, third, and fourth signals. A module coupled to the processor has logic instructions stored in a computer-readable medium, which configure the processor to analyze the signals to detect and classify the defects on the substrate.

Thus, the apparatus as described herein is able to simultaneously compare scattered radiation at two different angles of incidence, which enables the discrimination of different types of surface defects.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Described herein are exemplary systems and methods for detecting and classifying surface defects. In the following description, numerous specific details are set forth to provide a thorough understanding of various embodiments. However, it will be understood by those skilled in the art that the various embodiments may be practiced without the specific details. In other instances, well-known methods, procedures, components, and circuits have not been described in detail so as to not obscure the particular embodiments.

Various methods described herein may be embodied as logic instructions on a computer-readable medium. When executed on a processor the logic instructions cause a processor to be programmed as a special-purpose machine that implements the described methods. The processor, when configured by the logic instructions to execute the methods described herein, constitutes structure for performing the described methods.

The various embodiments of the system described herein enable the detection and classification of shallow bumps or dips in the surface of a substrate. In some embodiments the substrate surface is inspected at two different peak wavelengths using a scatterometer, having a first radiation beam with a peak wavelength at about four hundred and five nanometers, and a second radiation beam with a peak wavelength at about six hundred and sixty nanometers. The scatterometer is combined into a single system with a reflectometer, an optical phase tool, and a profilometer. In addition to the above capabilities, the tool has the ability to measure the polar Kerr effect (on magnetic disks) and is equipped with a micro-roughness blind scatterometer channel, as depicted in FIG. 5 (and described in U.S. Pat. No. 6,034,776, the entirety of the disclosure of which is incorporated herein by reference).

Figure 1:
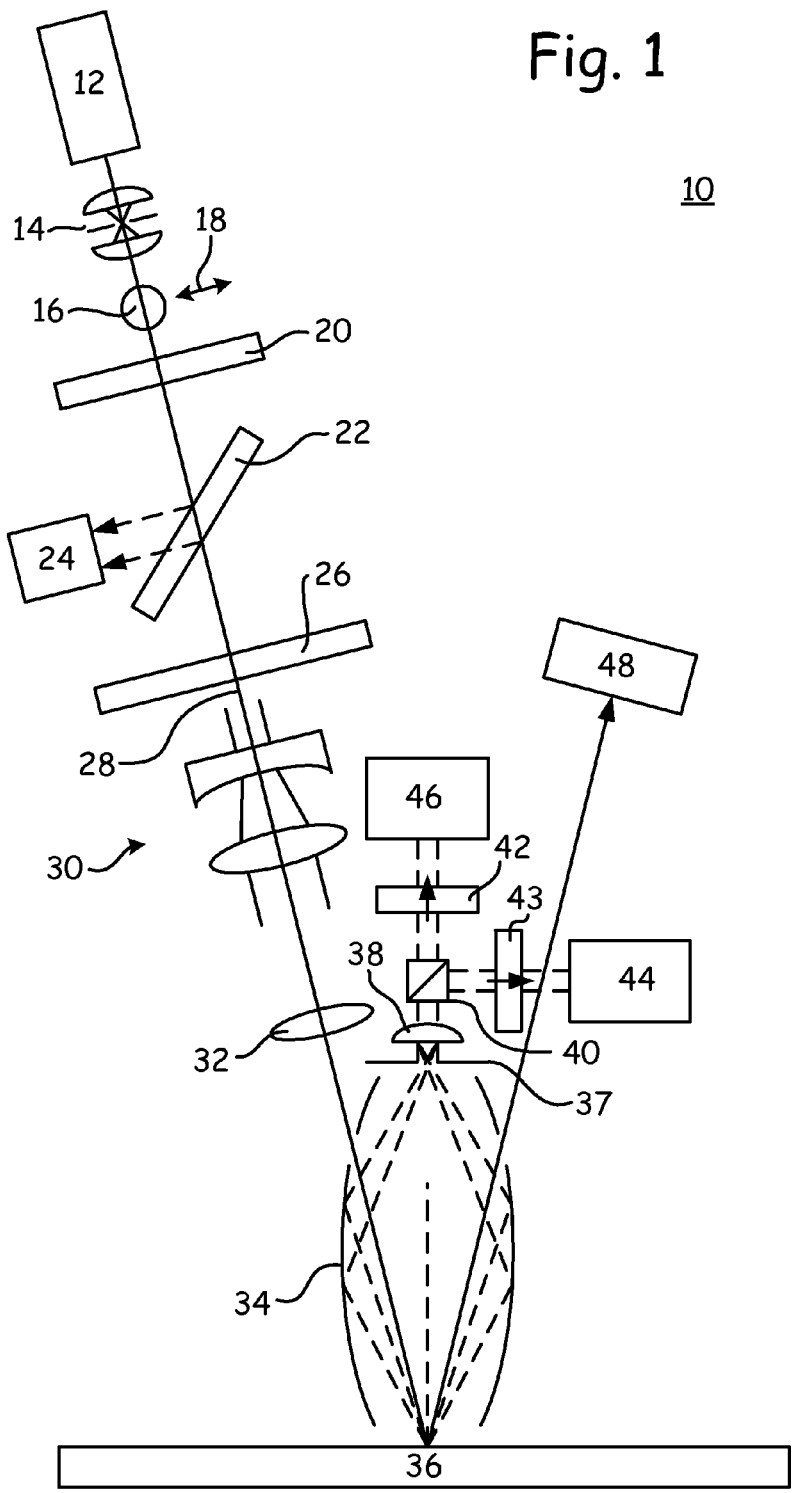
FIG. 1 is a schematic illustration of the components of an apparatus that direct a so-called near-normal incident beam onto a substrate according to an embodiment of the present invention.
Figure 2:
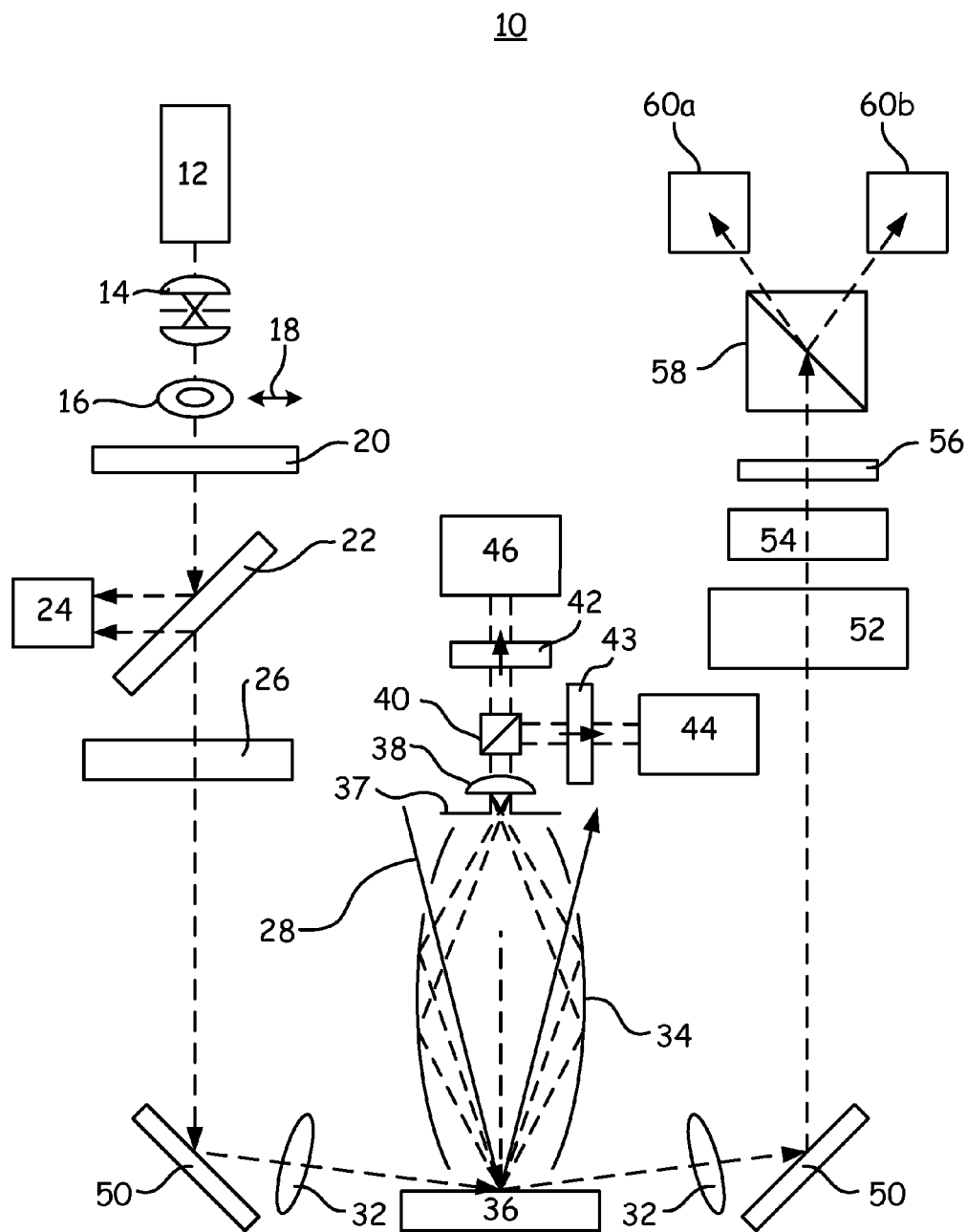
FIG. 2 is a schematic illustration of the components of an apparatus that direct a so-called obliquely incident beam onto a substrate according to an embodiment of the present invention.

FIG. 1 is a functional block diagram of an embodiment of an apparatus 10 to detect and classify surface defects on a substrate 36. The components described in regard to FIG. 1 direct a so-called near-normal incident beam onto a substrate 36. In various embodiments, these components are used either separately from or in conjunction with the components as depicted in FIG. 2, which direct a so-called obliquely incident beam onto the substrate 36. Thus, in some embodiments, the components of FIG. 1 and FIG. 2 are contained within the same apparatus 10. The two sets of components are depicted in separate figures herein, so as to not unnecessarily encumber the drawings. The planes of incidence of FIGS. 1 and 2 are orthogonal in some embodiments.

In the embodiment depicted in FIG. 1, the beam source 12 is, for example, a one hundred milliwatt, 660 nanometer (nominally red), one millimeter diameter laser beam source. The beam passes through a spatial filter 14, with a round beam shape 16, and with a linear polarization 18. The beam is passed through a switchable neutral density filter 20, and onto a beam splitter 22, which directs a portion of the beam toward a photo detector 24 that acts as a power monitor sensor. Portions of the beam pass through the beam splitter 22, and pass through a half wave plate 26, which rotates the polarization of the beam as desired.

The beam 28 that exits the half wave plate 26 has no more than about a thirty degree incidence angle (as measured from normal) on the substrate 36, where the plane of incidence is in the radial direction. A Galilean telescope 30 is employed to expand the beam from the nominal one millimeter diameter to about 7.8 millimeters, and lenses 32, such as GPX 10-40 (manufactured by Lightpath, Inc.), focus and collimate the beam onto the substrate 36, through apertures in a reflective ellipsoid of revolution 34 having a mirrored internal surface.

A portion of the beam is specularly reflected off of the substrate 36, back through additional apertures in the ellipsoid of revolution 34, and impinges on a beam dump 48. Another portion of the beam is scattered into the ellipsoid of revolution 34, and directed through a pinhole spatial filter 37 located at the second (top) foci of the ellipsoid of revolution 34, toward a condenser lens 38, and into a dichroic mirror 40. The dichroic mirror 40 directs a portion of the scattered light from the ellipsoid of revolution 34 through a color or band pass filter 42 that passes a wavelength of about 660 nanometers, which portion of the scattered light is then collected by a photomultiplier tube 46, such as is manufactured by Hamamatsu, Inc. The dichroic mirror 40 also directs a portion of the scattered light from the ellipsoid of revolution 34 through another color or band pass filter 43 that passes a wavelength of about 405 nanometers (nominally violet), which portion of the scattered light is then collected by another photomultiplier tube 44. The light at this wavelength comes from the components as described below in regard to FIG. 2.

With reference now to FIG. 2, there are described the components that direct a so-called obliquely incident beam onto a substrate 36. Components in FIG. 2 that are similar to the components as described above in regard to FIG. 1 are given the same reference number. However, it is appreciated that even though two components are similar and share a common reference number between the two drawings, the two components are not necessarily the same component, but in some embodiments might be two separate—but similar—components.

In the embodiment depicted in FIG. 2, the beam source 12 is, for example, a fifty milliwatt, constant power, 405 nanometer (nominally violet), laser beam source that produces an elliptical beam with a size of about four millimeters by about two millimeters. The beam passes through a spatial filter 14, with an elliptical beam shape 16, and with a P polarization 18. The beam is passed through a switchable neutral density filter 20, and onto a beam splitter 22 with an orientation at about 45 degrees, which directs a portion of the beam toward a photo detector 24 for power detection and monitoring. Portions of the beam pass through the beam splitter 22, and pass through a half wave plate 26, which rotates the polarization of the beam as desired.

The beam is reflected off of a turning mirror 50, and through focusing and collimating lenses 32 onto the substrate 36. When the beam impinges on the substrate 36, it is at an angle of about seventy degrees from normal, or about twenty degrees from the plane of the substrate 36.

A portion of the beam is specularly reflected off of the substrate 36, back through additional focusing and collimating lenses 32, turning mirror 50, and through a remote pinhole spatial filter 52. From there the reflected beam passes through a neutral density filter 54, a quarter waveplate 56, and splits through a Wollaston prism 58 that is rotated at about forty-five degrees to the plane of the paper onto phase, slope, and specular detectors 60a and 60b. Specular detectors 60a and 60b are quadrant detectors in one embodiment, wherein the signal difference between alternate pairs of such detectors indicates the slope of the surface of the substrate 36 in the circumferential and radial directions. The surface slope can then be integrated to yield the surface profile (topography) of the substrate 36.

Another portion of the beam is scattered into the ellipsoid of revolution 34, and directed through a pinhole spatial filter 37 located at the second (top) foci of the ellipsoid of revolution 34, toward a condenser lens 38 and into a dichroic mirror 40. The dichroic mirror 40 directs a portion of the scattered light from the ellipsoid of revolution 34 through a color or band pass filter 43 that is sensitive to a wavelength of about 405 nanometers (nominally violet), which portion of the scattered light is then collected by a photomultiplier tube 44. The dichroic mirror 40 directs another portion of the scattered light in the ellipsoid of revolution 34 through another color or band pass filter 42 that is sensitive to a wavelength of about 660 nanometers (nominally red), which portion of the scattered light is then collected by another photomultiplier tube 46. The light at this wavelength comes from the components as described above in regard to FIG. 1, as originating from the beam 28. In some embodiments, the oblique laser beam is incident in the circumferential plane and the near-normal laser beam is incident in the radial plane.

The two color beam configuration allows the collection of both red and violet scatter in a single pass. When the configuration as depicted in FIGS. 1 and 2 is combined into a single system 10 with a micro-roughness blind scatterometer, the system 10 is capable of discriminating a pure pit from a pit with an internal peak. In some embodiments, this system 10 is used to implement a method for separating pits, particles, and shallow bumps. In addition, the system 10 can be used to implement a method of discriminating a pure pit from a pit with an internal peak. Further, these methods can be applied to defects with lateral dimensions of less than half a micron in diameter.

Figure 5A:
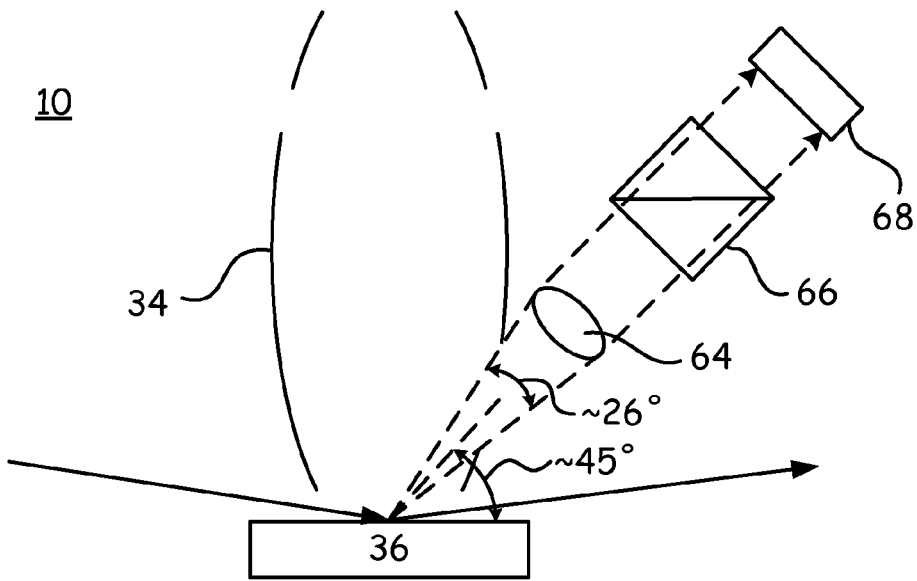
FIG. 5A is side-view schematic illustration of the components of an apparatus that receive scattered light from an obliquely incident beam and separates it into a surface roughness scattered component and a particle scattered component according to an embodiment of the present invention.
Figure 5B:
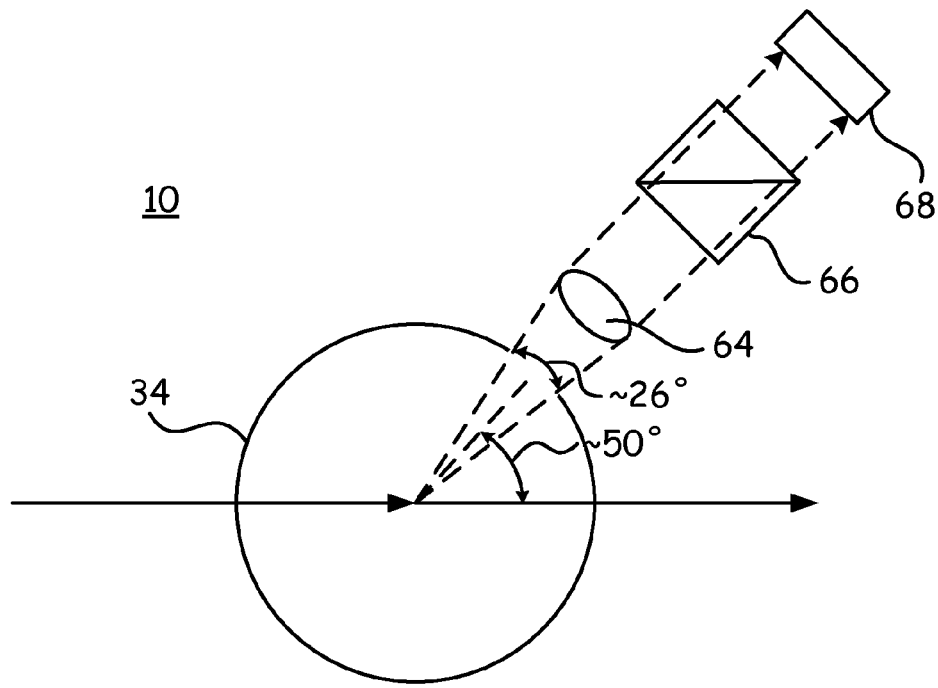
FIG. 5B is top-view schematic illustration of the components of an apparatus that receive scattered light from an obliquely incident beam and separates it into a surface roughness scattered component and a particle scattered component according to an embodiment of the present invention.

An embodiment of the micro-roughness blind scatterometer components of the apparatus 10 is shown in FIGS. 5A and 5B, where FIG. 5A is a side view and FIG. 5B is a top view of the components. The micro-roughness blind scatterometer components are used to separate the scattered signal that is generated by the surface micro-roughness from the scattered signal that is generated by the particles residing on the top of the surface of the substrate 36. An oblique beam is directed toward the surface of the substrate at an angle of incidence of about seventy degrees from normal. A small hole in the ellipsoid of revolution 34 allows scattered light to exit the ellipsoid 34 at an elevation of about forty-five degrees and an azimuth of about fifty degrees.

The scattered light that exits the hole is a blend of two components of light. A first component is the light that is scattered due to surface roughness of the substrate 36, and a second component is the light that is scattered due to particulate matter on the surface of the substrate 36. When the incident beam is P polarized, then these two components have different polarizations. The light that is scattered due to surface roughness is substantially S polarized. The light that is scattered due to particles is substantially P polarized. The scattered light is collected with a lens 64 and directed through a polarizer 66 the separates the surface roughness scattered light (S polarized) from the particle scattered light (P polarized). The desired component of the light is collected with a photomultiplier 68. In this manner, the surface roughness signal is substantially separated from the particle signal. This scattered light can also be used to separate flat particles, particles, and pits.

Figure 3:
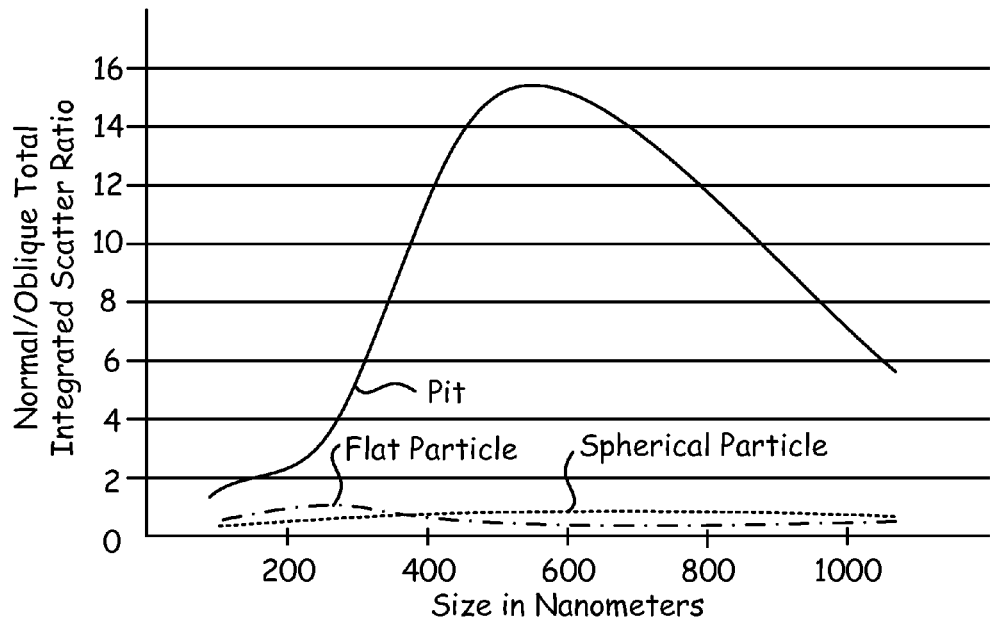
FIG. 3 is a graph depicting the normal/oblique total integrated scatter amplitude ratio for flat particles, pits, and spherical particles in S polarization.
Figure 4:
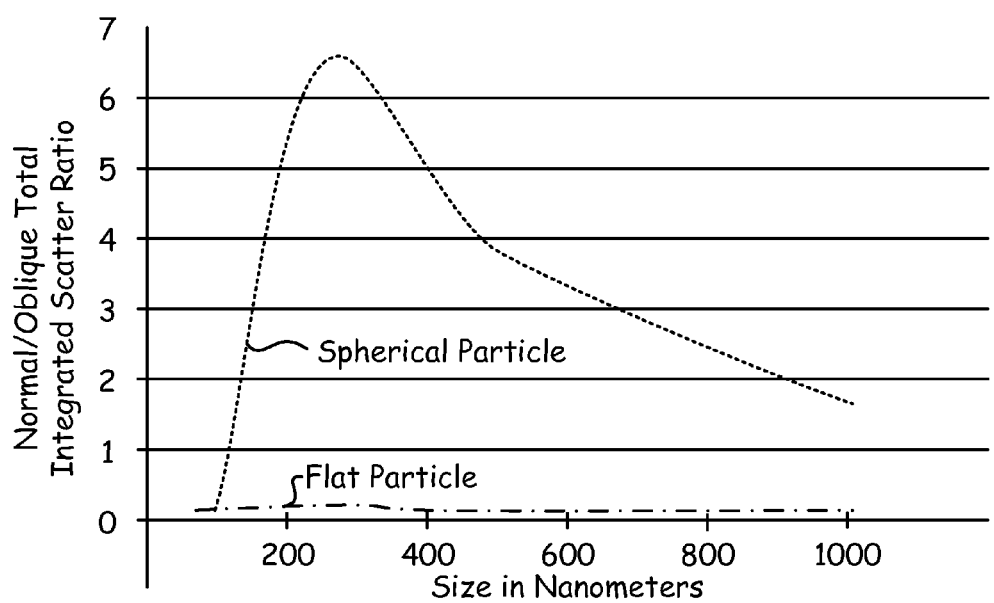
FIG. 4 is a graph depicting the normal/oblique total integrated scatter amplitude ratio for flat particles and spherical particles in P polarization.

FIG. 3 depicts the theoretical normal/oblique total integrated scatter amplitude ratio for flat particles, pits, and spherical particles in S polarization, versus the diameter of the defect. At larger diameters, greater than about half a micron, it is easy to use this ratio to separate pits from flat particles and spherical particles. However, it is more challenging to differentiate spherical particles from flat particles (bumps with a shallow slope). FIG. 4 depicts the same ratio versus lateral size for P polarization. In this case it is quite easy to separate spherical particles from flat particles.

In one embodiment, the normal/oblique total integrated scatter amplitude ratio is first measured when scanning the surface using radiation in S polarization to separate pits from spherical particles and flat particles, as depicted in FIG. 3. The polarization is then changed to P and the sample is rescanned and the remaining spherical or non-spherical particles and flat particles are placed in separate classifications using the P polarization normal/oblique ratio, as depicted in FIG. 4. In some embodiments the normal/oblique ratio is measured and recorded with radiation in the S polarization for all of the defects. If the ratio for a given defect exceeds about three, then that defect is classified as a pit (as seen in FIG. 3), and the S ratio values for all of the other defects is recorded. The sample is then rescanned in P polarization, and an observation is made as to which of the defects had an increase in ratio. Those defects are classified as particles (as seen in FIG. 4). Those defects that had a decrease in ratio are classified as flat particles. In this manner, pits, spherical or non-spherical particles, and flat particles are all classified by a single instrument.

A pure pit, that is, one which has its surface always extending below the mean plan of the substrate, is distinguished from a pit with a peak sticking up from the bottom of the pit by using the normal/oblique ratio and the micro-roughness blind scatter channel. A pure pit has a large normal/oblique ratio and a small micro-roughness blind scatter (since nothing sticks above the surface) and a pit with a peak sticking up from the bottom has a large normal/oblique ratio and a large micro-roughness blind scatter (since the part sticking up past the surface of the substrate appears particle-like). In this manner these different types of pits are distinguished.

The above discussion relates to defects with lateral dimensions greater than about a half micron in diameter. When the diameters reduce below these dimensions, it becomes more difficult in practice to distinguish pits, spherical or non-spherical particles, and flat particles.

Figure 6:
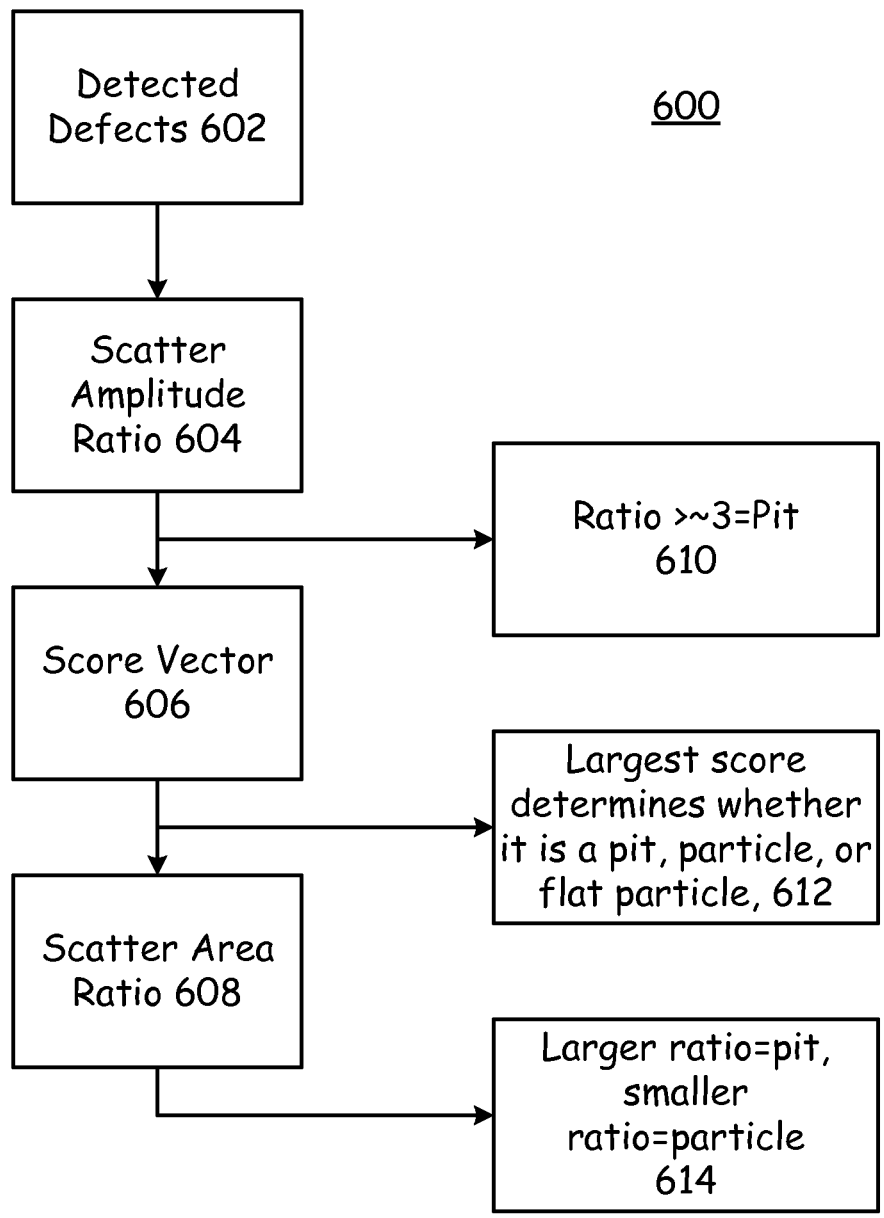
FIG. 6 is a flow chart depicting an embodiment of the present invention.

In one embodiment of a method 600 as illustrated in FIG. 6, the scatter amplitude ratio is first used to separate pits with lateral dimensions that are greater than about a half micron in diameter from all of the other detected defects. The general method is to input the data from the detected defects as given in block 602, and compute a scatter amplitude ratio as given in block 604. If the ratio is above about three, the defect is designated as a pit as given in block 610. In such a case, the pit is typically larger than about a half micron in diameter. The score vector for the other defects is then computed, as given in block 606. The largest score vector is used to determine whether the defect is a pit (smaller than about a half micron), particle, or flat particle, as given in block 612. The scatter area ratio is then determined, as given in block 608. Larger ratios are designated as pits (typically less than about a half micron in diameter), and smaller ratios are designated as particles, as given in block 614. The method described below provides more detail in regard to classifying defects having lateral dimensions in the range of from about two-tenths of a micron to about half a micron.

Table 1 summarizes the factors that tend to affect the scatter amplitude ratio. For both micro-pits and flat particles (also referred to as bumps in the art), the normal/oblique scatter amplitude ratio depends not only on the lateral size, but also on the height/depth of the defect. For defects that are a mixture of pit and bump, the ratio tends to lie between a pure pit and a flat particle of equal dimension.

TABLE 1

Factors that affect scatter amplitude ratio.

| | Pit | Flat Particle | Mixture (Bump and Pit) |
|---|---|---|---|
| Major Factors | Lateral Size Depth | Lateral Size Height | Lateral Size Height Depth |
| Minor Factors | Surface Roughness Shape Etc. | Surface Roughness Shape Etc. | Surface Roughness Shape Etc. |

Additional parameters may be used to separate pits, particles, and flat particles when the diameter is in the range of from about two-tenths of a micron to about half a micron. The parameters used include the normal/oblique scatter amplitude ratio change from S polarization to P polarization, defined as:

$$\left(\frac{(N/O \text{ Ratio})_{P \text{ Polarization}} - (N/O \text{ Ratio})_{S \text{ Polarization}}}{(N/O \text{ Ratio})_{S \text{ Polarization}}}\right),$$

ratio over normal peak amplitude in S polarization, defined as:

$$\left(\frac{(N/O \text{ Ratio})_{S \text{ Polarization}}}{(N \text{ Peak Amplitude})_{S \text{ Polarization}}}\right),$$

and the micro-roughness blind scatter.

Pits in the range of from about two-tenths of a micron to about half a micron do not show a consistent response in ratio change. However, they consistently present small values for both the ratio over normal peak amplitude in S polarization and the micro-roughness blind scatter. Particles and spherical particles demonstrate a positive ratio change when the polarization is changed from S to P, a small value for ratio over normal peak amplitude in S polarization, and a large micro-roughness blind scatter. Flat particles demonstrate a negative ratio change when the polarization is changed from S to P, and little micro-roughness blind scatter response. These three parameters are combined into a score vector that is summarized in Table 2. By analyzing the parameter values of a defect, a score is assigned under each defect type to indicate how probable it is that the defect is accurately classified as the given defect type. Higher scores suggest larger probabilities. For simplicity, the defect is classified as the defect type that is assigned the highest score. In this manner, pits, particles, and flat particles in the range of from about two-tenths of a micron to about half a micron in diameter are classified.

TABLE 2

Score vector for various defects.

|  | Scatter Amplitude Ratio Range | Ratio Over Normal Peak Amplitude | Micro Roughness Blind Scatter |
|---|---|---|---|
| <Half Micron Pit | Mixed | Small (mostly) | Small |
| Particles | Negative | Small | Large |
| Flat Particles | Positive | Large | No Signal (Mostly) |
| Mixture Pit & Bump | Mixed | Mixed | Mixed |

Table 3 provides an example of the score vector for three different defects. By combining the scattered light from three different scatter channels, this presents a method and apparatus to detect and classify pits, particles, and flat particles with lateral dimensions greater than about two-tenths of a micron.

TABLE 3

Classification by score vector.

|  | Flat Particle | Spherical Particle | Pit |  |
|---|---|---|---|---|
| Defect 1 | 1.1 | 2 | 1.4 | → Particle |
| Defect 2 | 2.3 | 0 | 1.6 | → Flat Particle |
| Defect 3 | 1 | 1 | 1.5 | → Pit |

Based on the response of different defect types in all the parameters used, an algorithm is implemented to calculate a score vector for each defect. Referring to Table 3, samples of score vectors are shown. A higher score indicates a higher probability of being the corresponding defect type. Thus, in one embodiment as illustrated in FIG. 6, the defect may be classified as the type with the highest score in the score vector.

In those cases where a highest score cannot be determined, such as when equal scores are obtained for two or more types, the normal/oblique scatter area ratio and normal/micro roughness blind scatter area ratio are used to determine the classification. A pit has a larger scatter area ratio as compared to a particle of a similar lateral dimension. The scatter area ratio difference between a pit and a particle, however, decreases as their lateral dimension increases. Therefore, considering the lateral dimension of a defect, different thresholds are applied to the scatter area ratio to determine if the defect is a pit or a particle.

Figure 7:
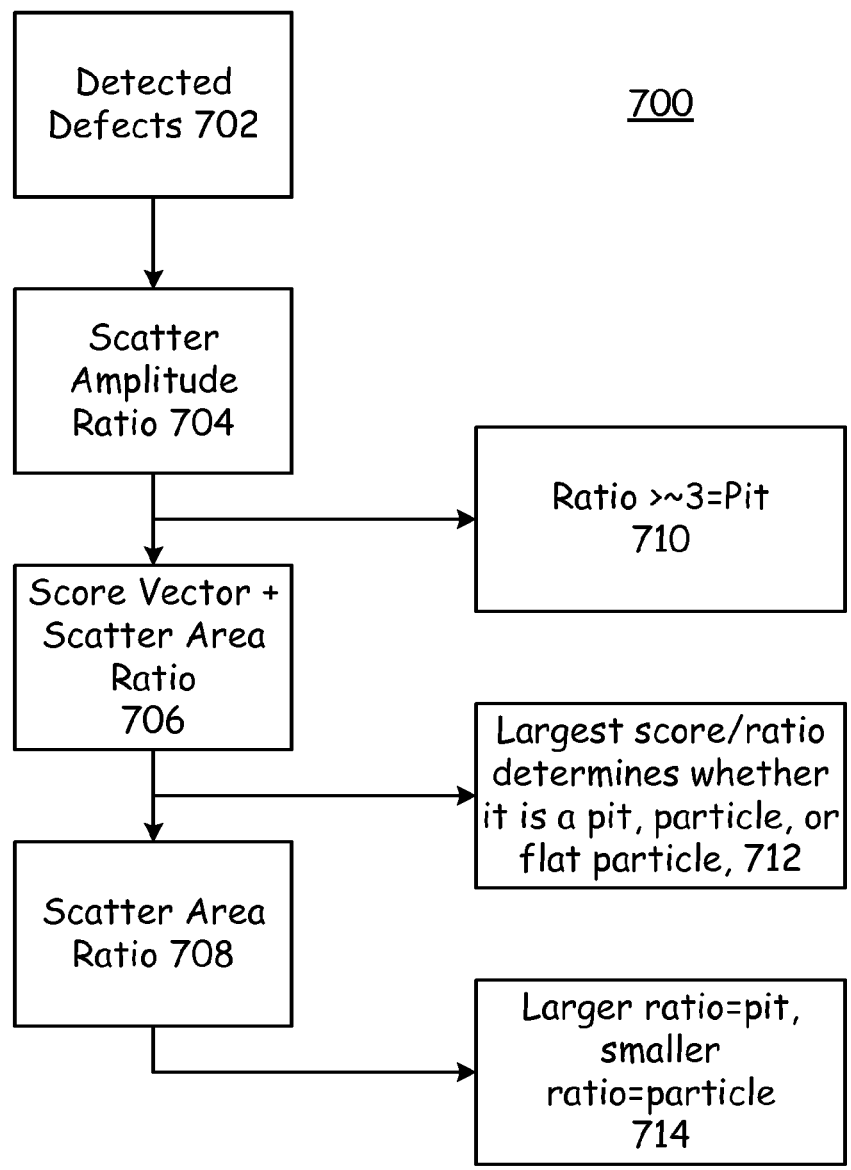
FIG. 7 is a flow chart depicting another embodiment of the present invention.

In the embodiment depicted in FIG. 7, a score vector and a scatter area ratio are used to classify the defects in the range of from about two-tenths of a micron to about half a micron in diameter. Defects with unusual shapes, mixture of height and depth, and so forth can have an atypical response in the parameters that are used to determine the score vectors. The scatter area ratio can be loosely used to eliminate cases where the score vector doesn't provide a pronounced classification result. The scatter area ratio is then used in a more stringent manner to classify the remaining challenging score vector defects.

As generally depicted in FIG. 7, the basic flow of the method 700 is to input the data from the detected defects as given in block 702, and compute a scatter amplitude ratio as given in block 704. If the ratio is above about three, the defect is designated as a pit as given in block 710. In such a case, the pit is typically larger than about a half micron in diameter. The score vector and scatter area ratio for the other defects is then computed, as given in block 706. The largest score vector and area ratio is used to determine whether the defect is a pit (smaller than about a half micron), particle, or flat particle, as given in block 712. The scatter area ratio as given in block 708 is then used, where larger area ratios are designated as pits (typically less than about a half micron in diameter), and smaller ratios are designated as particles, as given in block 714.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An apparatus to detect and classify defects on a surface of a substrate, comprising:
    an ellipsoid of revolution disposed over the substrate, having first and second open ends with first and second loci at the first and second open ends respectively, a reflective interior, and separate first, second, and third apertures,
    a first radiation targeting assembly to direct first radiation having a first peak wavelength in a first beam along a first path between the ellipsoid of revolution and the substrate and onto the surface of the substrate at the position of the first locus, thereby forming a specularly reflected first beam that leaves the surface of the substrate along a path between the ellipsoid of revolution and the substrate, and also forming scattered first radiation that is reflected by the ellipsoid of revolution to the second locus,
    a second radiation targeting assembly to direct second radiation having a second peak wavelength in a second beam along a second path through the first aperture in the ellipsoid of revolution and onto the surface of the substrate at the position of the first locus, thereby forming a specularly reflected second beam that leaves the surface of the substrate along a path through the second aperture of the ellipsoid of revolution, and also forming scattered second radiation that is reflected by the ellipsoid of revolution to the second locus,
    where
        the first beam and the second beam are directed onto the surface of the substrate simultaneously, the first radiation targeting assembly is separate from the second radiation targeting assembly, and the first peak wavelength is different from the second peak wavelength, a first radiation collecting assembly to collect the specularly reflected first beam and produce first signals, a second radiation collecting assembly to collect first radiation from the second locus and produce second signals, a third radiation collecting assembly to collect second radiation from the second locus and produce third signals, a fourth radiation collecting assembly to selectively collect one of, first scattered radiation through the third aperture, second scattered radiation through the third aperture, and first and second scattered radiation through the third aperture, and produce fourth signals, a processor coupled to the first, second, third, and fourth radiation collecting assemblies, for receiving the first, second, third, and fourth signals, a memory module coupled to the processor and comprising logic instructions stored in a computer-readable storage medium, which when executed by the processor configure the processor to, record the first, second, third, and fourth signals, and analyze the first, second, third, and fourth signals to detect and classify defects on the surface of the substrate.

2. The apparatus of claim 1, wherein the second radiation targeting assembly directs the second beam onto the surface of the substrate at an incidence angle that is no more than thirty degrees from normal to the surface of the substrate.

3. The apparatus of claim 1, wherein the first radiation targeting assembly directs the first beam onto the surface of the substrate at an incidence angle that is greater than fifty degrees from normal to the surface of the substrate.

4. The apparatus of claim 1, wherein the first peak wavelength is four hundred and five nanometers.

5. The apparatus of claim 1, wherein the second peak wavelength is six hundred and sixty nanometers.

6. The apparatus of claim 1, wherein the logic instructions further configure the processor to compare a ratio comprised of at least one of the combinations including: the fourth signal with the third signal, the fourth signal with the second signal, the third signal with the second signal, the third and fourth signals with the first and second signals, the third signal with the first and second signals, the fourth signal with the first and second signals, the third and fourth signals with the first signal, the third and fourth signals with the second signal, the third signal with the first signal, the third signal with the second signal, the fourth signal with the first signal, and the fourth signal with the second signal.

7. The apparatus of claim 6 where the ratio is based at least in part on amplitudes of the signals.

8. The apparatus of claim 6 where the ratio is based at least in part on scatter areas represented by the signals, where the scatter areas are determined by where the signals exceed a threshold.

9. The apparatus of claim 1, wherein the first radiation is in a first polarization state and the second radiation is in a second polarization state, where the first polarization state is different from the second polarization state.

10. The apparatus of claim 1, wherein the logic instructions further configure the processor to compare a change between:

a first ratio comprised of at least one of the combinations including: the fourth signal with the third signal, the fourth signal with the second signal, the third signal with the second signal, the third and fourth signals with the first and second signals, the third signal with the first and second signals, the fourth signal with the first and second signals, the third and fourth signals with the first signal, the third and fourth signals with the second signal, the third signal with the first signal, the third signal with the second signal, the fourth signal with the first signal, and the fourth signal with the second signal, where the radiation is in a first polarization state, and a second ratio comprised of the same combination as the first ratio, where the radiation is in a second polarization state, where the first polarization state is different from the second polarization state.

\* \* \* \* \*